US011730629B2

(12) United States Patent
Becker et al.

(10) Patent No.: US 11,730,629 B2
(45) Date of Patent: Aug. 22, 2023

(54) SMART WELDING HELMETS

(71) Applicant: Illinois Tool Works Inc., Glenview, IL (US)

(72) Inventors: William Joshua Becker, Manitowoc, WI (US); Joseph C. Schneider, Greenville, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 17/488,953

(22) Filed: Sep. 29, 2021

(65) Prior Publication Data
US 2022/0133542 A1 May 5, 2022

Related U.S. Application Data

(60) Provisional application No. 63/109,036, filed on Nov. 3, 2020.

(51) Int. Cl.
| | | |
|---|---|---|
| *A61F 9/06* | (2006.01) | |
| *G05B 9/02* | (2006.01) | |
| *G08B 7/06* | (2006.01) | |
| *G08B 21/02* | (2006.01) | |
| *G08B 25/01* | (2006.01) | |

(52) U.S. Cl.
CPC ............... *A61F 9/06* (2013.01); *G05B 9/02* (2013.01); *G08B 7/06* (2013.01); *G08B 21/02* (2013.01); *G08B 25/016* (2013.01)

(58) Field of Classification Search
CPC .... A61F 9/06; G05B 9/02; G08B 7/06; G08B 21/02; G08B 25/016
See application file for complete search history.

(56) References Cited

U.S. PATENT DOCUMENTS

| | | |
|---|---|---|
| 6,614,409 B1 | 9/2003 | Bae |
| 6,853,303 B2 | 2/2005 | Chen et al. |
| 8,207,858 B2 | 6/2012 | Knopf et al. |

(Continued)

FOREIGN PATENT DOCUMENTS

CN 106510942 A * 3/2017

OTHER PUBLICATIONS

Tran et al., A fully automated vision-based system for real-time personal protective detection and monitoring, ResearchGate, Nov. 2019, 7 pages.

(Continued)

*Primary Examiner* — Brian Wilson
(74) *Attorney, Agent, or Firm* — McAndrews, Held & Malloy, Ltd.

(57) ABSTRACT

Described herein are examples of smart welding helmets having a plurality of functions that go beyond conventional welding helmets. For example, a smart welding helmet may be configured to detect if/when the helmet surpasses one or more temperature thresholds, which may alert an operator if they have been welding too close and/or for too long. Other example smart helmet functions may include the ability to display (and/or otherwise output) feedback/guidance and/or welding information, as well as communicate with appropriate personnel. In some examples, the smart welding helmet may be configured to selectively enable/disable certain functions of the smart welding helmet to accommodate the needs of a particular operator and/or groups of operators.

20 Claims, 6 Drawing Sheets

(56) References Cited

U.S. PATENT DOCUMENTS

| | | | |
|---|---|---|---|
| 8,208,681 | B2 | 6/2012 | Heller et al. |
| 8,294,580 | B2 | 10/2012 | Witwer et al. |
| 8,842,019 | B2 | 9/2014 | Boccola |
| 9,207,468 | B2 | 12/2015 | Davalos et al. |
| 9,695,981 | B2 | 7/2017 | Au et al. |
| 9,998,804 | B2 | 6/2018 | Awiszus et al. |
| 10,395,499 | B2 | 8/2019 | Kritzler et al. |
| 2008/0082179 | A1* | 4/2008 | Yang ............ A61F 9/061 700/83 |
| 2014/0307076 | A1 | 10/2014 | Deutsch |
| 2015/0173445 | A1* | 6/2015 | Gordon ............ F25B 21/04 62/3.3 |
| 2017/0091698 | A1 | 3/2017 | Holler et al. |
| 2017/0169533 | A1 | 6/2017 | O'Brien |
| 2017/0248272 | A1* | 8/2017 | Ullrich ............ F16P 3/14 |
| 2017/0259089 | A1 | 9/2017 | De Jesus |
| 2018/0211345 | A1 | 7/2018 | Bean et al. |
| 2019/0175411 | A1 | 6/2019 | Awiszus |
| 2020/0146384 | A1 | 5/2020 | Egeland et al. |
| 2021/0085524 | A1 | 3/2021 | Huh |

OTHER PUBLICATIONS

Barro-Torres et al., A fully automated vision-based system for real-time personal protective detection and monitoring, Computer Communications, vol. 36, Dec. 2012, 11 pages.

Kelm et al., Mobile passive Radio Frequency Identification (RFID) portal for automated and rapid control of Personal Protective Equipment (PPE) on construction sites, Automation in Construction, vol. 36, Dec. 2013, 3 pages.

Smart-Tec; Creative RFID-Technology for your personal protective equipment (PPE), https://www.smart-tec.com/en, retrieved Sep. 2021, 9 pages.

Roy, Rupali; Using YOLOv3 for real-time detection of PPE and Fire, https://towardsdatascience.com/using-yolov3-for-real-time-detection-of-ppe-and-fire-1c671fcc0f0e, May 11, 2020, 15 pages.

Peniak, Martin; Real-time PPE Monitoring on the Edge powered by the latest ultra-low-power high-performance Intel Myriad X VPU, https://cortexica.github.io/intel-rrk-safety/, retrieved Sep. 2021, 13 pages.

Iomascolo; PPE automated detection to prevent risks at the workplace, https://pervasive-tech.com/blog/author/Iomascolo/, Jan. 26, 2020, 5 pages.

Delhi et al., Detection of Personal Protective Equipment (PPE) Compliance on Construction Site Using Computer Vision Based Deep Learning Techniques, frontiers in Built Environment, Sep. 24, 2020, 10 pages.

Sole et al., RFID Sensor Network for Workplace Safety Management, https://www.researchgate.net/publication/261334054, Sep. 2013, 5 pages.

RayReach Technologies; PPE Violation Detection, https://www.rayreachtech.com/, retrieved Sep. 2021, 4 pages.

Hatipoglu et al., Detection of personal protective equipment, IEEE, 2018, 2 pages.

European Patent Office, Partial European Search Report, application No. 21202506.8, dated Mar. 16, 2022, 13 pages.

\* cited by examiner

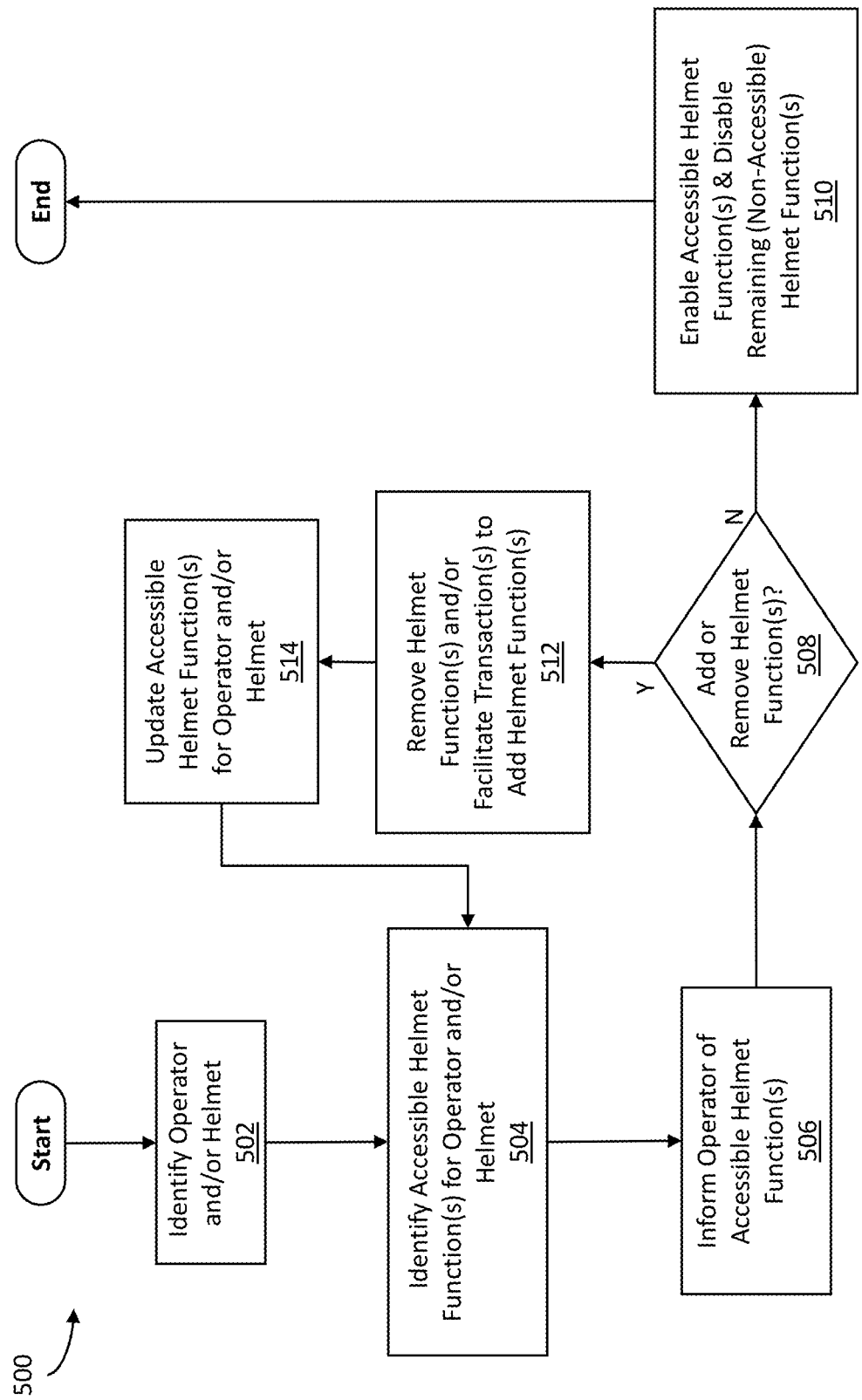

SMART WELDING HELMETS

CROSS REFERENCE TO RELATED APPLICATIONS

This application claims priority to, and the benefit of, U.S. Provisional Patent Application No. 63/109,036, entitled "SMART WELDING HELMETS," filed Nov. 3, 2020, the entire contents of which being hereby incorporated by reference.

TECHNICAL FIELD

The present disclosure generally relates to welding helmets and, more particularly, to smart welding helmets.

BACKGROUND

Conventional welding helmets are sometimes worn by welding when performing welding operations. The helmets have a hard shell configured to shield the head of an operator from welding spatter, and a viewing window so that the operator can see the surrounding environment while wearing the helmet. Some welding helmets are shared between operators, while others are reserved for use by only one operator.

Limitations and disadvantages of conventional and traditional approaches will become apparent to one of skill in the art, through comparison of such systems with the present disclosure as set forth in the remainder of the present application with reference to the drawings.

BRIEF SUMMARY

The present disclosure is directed to smart welding helmets, substantially as illustrated by and/or described in connection with at least one of the figures, and as set forth more completely in the claims.

These and other advantages, aspects and novel features of the present disclosure, as well as details of an illustrated example thereof, will be more fully understood from the following description and drawings.

BRIEF DESCRIPTION OF THE DRAWINGS

FIG. 5 is a flow diagram illustrating an example operation of a helmet function program of the smart helmet of FIG. 1, in accordance with aspects of this disclosure.

The figures are not necessarily to scale. Where appropriate, the same or similar reference numerals are used in the figures to refer to similar or identical elements.

DETAILED DESCRIPTION

Figure 1:
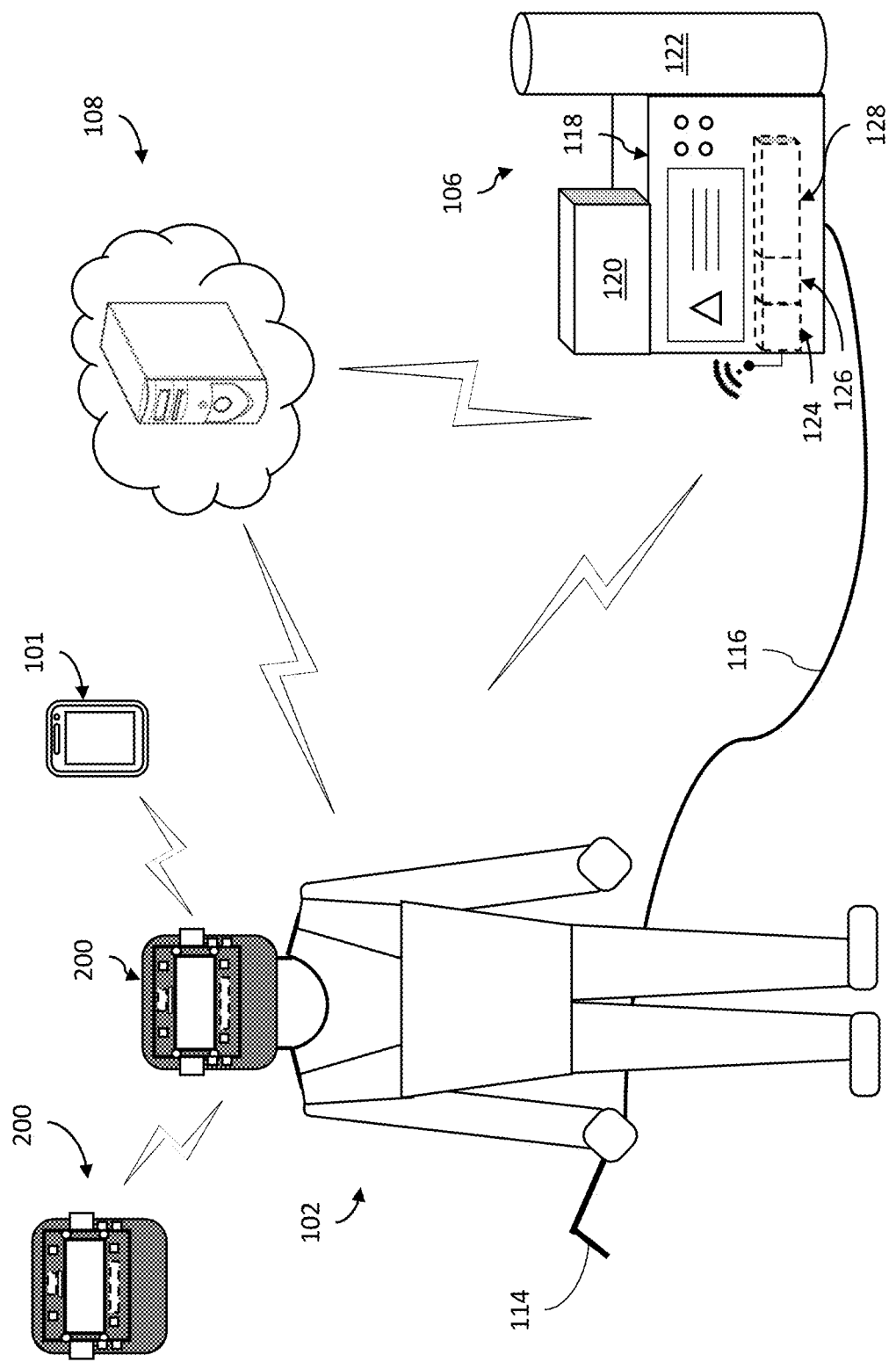
FIG. 1 shows an example of an operator wearing a smart welding helmet, in accordance with aspects of this disclosure.

Some examples of the present disclosure relate to smart welding helmets. In some examples, a smart welding helmet may have bevy of helmet functions that go beyond the normal capabilities of a conventional welding helmet. For example, a smart welding helmet may be configured to detect if/when the helmet surpasses one or more temperature thresholds, which may alert an operator if they have been welding too close and/or for too long. Other example smart helmet functions may include the ability to display (and/or otherwise output) feedback/guidance and/or welding information, as well as communicate with appropriate personnel. In some examples, the smart welding helmet may be configured to selectively enable/disable certain functions of the smart welding helmet to accommodate the needs of a particular operator and/or groups of operators.

Some examples of the present disclosure relate to a welding helmet, comprising: an outer shell having an external surface; a cover lens having an outer surface; a temperature sensor configured to measure a temperature indicative of the external surface of the outer shell or the outer surface of the cover lens; and control circuitry configured to output a signal in response to determining the temperature exceeds a threshold.

In some examples, the signal indicates a risk to the welding helmet due to high temperature. In some examples, the welding helmet further comprises a user interface configured to receive the signal and output a visual notification or audible notification in response to receiving the signal. In some examples, the visual notification or audible notification indicates a risk to the welding helmet due to high temperature.

In some examples, the control circuitry is configured to output the signal to an external device via communication circuitry. In some examples, the external device is a mobile device. In some examples, the external device is a computer. In some examples, the external device is a piece of welding equipment, and the signal comprises a disable signal.

In some examples, the temperature sensor is integrated into the cover lens. In some examples, the welding helmet further comprises a thermal conductor extending from the external surface of the outer shell into an interior of the outer shell, the temperature sensor being positioned proximate the thermal conductor.

Some examples of the present disclosure relate to a welding helmet, comprising: control circuitry configured to: identify one or more helmet functions of a plurality of helmet functions that are accessible, and enable the one or more helmet functions and disable a remainder of the plurality of helmet functions.

In some examples, the control circuitry is configured to determine an identity of an operator wearing the welding helmet, and identify the one or more helmet functions that are accessible based on the identity of the operator. In some examples, the welding helmet further comprises a sensor configured to automatically detect a characteristic of the operator, the control circuitry configured to determine the identity of the operator based on the characteristic detected by the sensor. In some examples, the welding helmet further comprises a user interface configured to receive credentials of the operator, the control circuitry configured to determine the identity of the operator based on the credentials received by the user interface.

In some examples, welding helmet further comprises a user interface configured to output a notification to an operator wearing the welding helmet identifying the one or more helmet functions that are accessible. In some examples, the plurality of helmet functions comprise two or more of a helmet status detection function, an automatic light configuration function, an automatic lens configuration function, a torch travel speed detection function, a temperature detection function, a personal protective equipment (PPE) detection function, an arc on time tracking function, an operator identification function, a lens maintenance detection function, a welding parameter viewing function, a work instruction viewing function, a communication function, or a guidance or feedback function.

In some examples, the control circuitry is configured to identify the one or more helmet functions based on one or more signals received from an external device. In some examples, the control circuitry is configured to identify the one or more helmet functions based on a file or data structure stored in memory circuitry of the welding helmet. In some examples, the welding helmet further comprises communication circuitry configured to communicate with an external device, the control circuitry configured to update the file or data structure based on one or more signals received from the external device via the communication circuitry. In some examples, the update comprises a change in the one or more helmet functions that are accessible.

FIG. 1 shows an example of a welding operator 102 wearing a smart welding helmet 200. As shown, the smart welding helmet 200 is in communication with welding equipment 106, one or more mobile devices 101 (e.g., smartphones, tablets, etc.), one or more other smart welding helmets 200, and one or more remote servers 108. While referred to as remote, in some examples one or more of the remote servers 108 may be nearby servers and/or (e.g., desktop, laptop, etc.) computers. In some examples, the smart welding helmet 200 may also be in communication with other welding devices, such as, for example, a welding torch 114 connected to the welding equipment 106 via cable 116. In some examples, some or all of the communication may be through one or more cellular communication networks, local area networks, and/or wide area networks (e.g., the Internet).

In the example of FIG. 1, the welding equipment 106 comprises a welding-type power supply 118, wire feeder 120, and gas supply 122. In some examples, the wire feeder 120 may be configured to feed wire to the welding torch 114. In some examples, the gas supply 122 may be configured to route shielding gas to the welding torch 114.

In the example of FIG. 1, the power supply 118 includes communication circuitry 124, control circuitry 126, and power conversion circuitry 128 interconnected with one another. In some examples, the communication circuitry 124 may be configured for communication with the remote server(s) 108, welding torch 114, and/or the smart welding helmet 200. In some examples, the power conversion circuitry 128 may be configured to receive input power (e.g., from a generator, a battery, mains power, etc.) and convert the input power to welding-type output power, such as might be suitable for use by the welding torch 114 for welding-type operations, for example. In some examples, the control circuitry 126 may be configured to control operation of the communication circuitry 124, power conversion circuitry 128, wire feeder 120, and/or gas supply 122 (e.g. via one or more control signals). In some examples, the control circuitry 126 may control communications of the welding equipment 106 with the smart helmet 200.

Figure 2A:
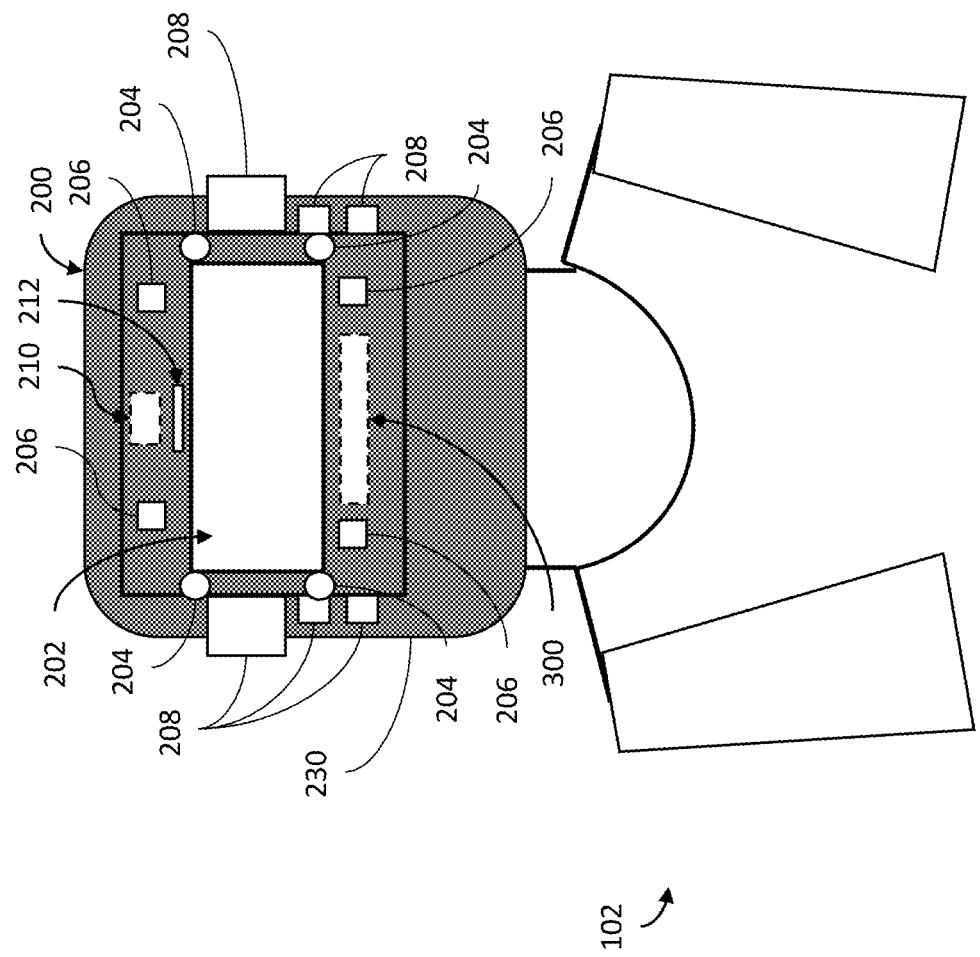
FIG. 2a shows an enlarged front view of the smart welding helmet of FIG. 1, in accordance with aspects of this disclosure.
Figure 2B:
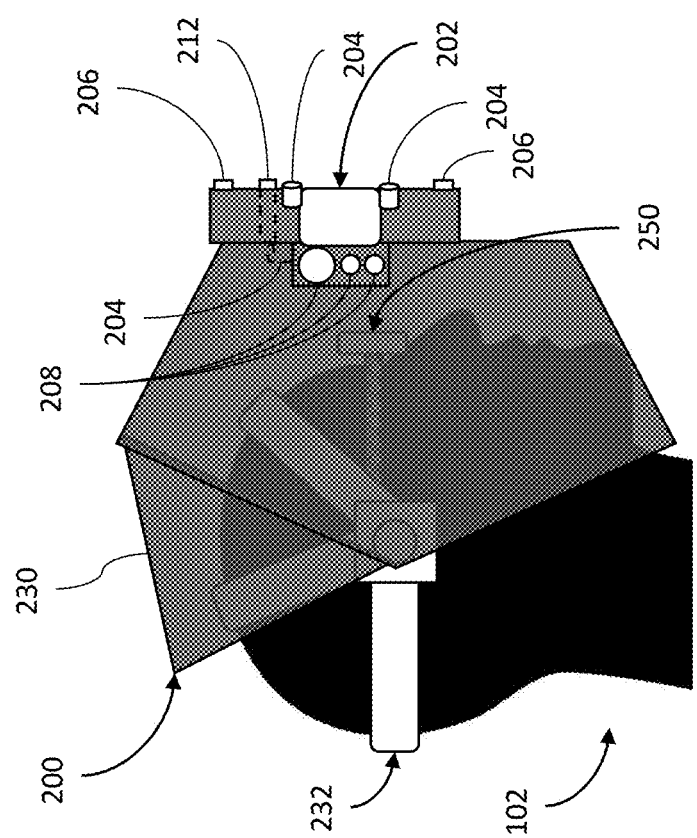
FIG. 2b shows a side view of the example smart welding helmet of FIG. 1, in accordance with aspects of this disclosure.

FIGS. 2a-2b show enlarged front and side depictions of the example smart welding helmet 200. As shown, the smart welding helmet 200 comprises a helmet shell 230 attached to a suspension 232. As shown, the suspension 232 comprises several straps and/or bands configured to wrap around the head of an operator 102. The straps are connected to one another and to the helmet shell 230 at least at two side attachment points on either side of the head of the operator 102. In some examples, the smart helmet 200 may be configured to rotate and/or pivot about the side attachment points to transition between raised and lowered positions.

In the example of FIGS. 2a-2b, the smart helmet 200 includes a cover lens 202, several sensors 204, multiple lights 206, a thermally conductive element 212, a plurality of control inputs 208 (e.g., knobs, buttons, levers, switches, touch screens, microphones, etc.), helmet circuitry 300 (e.g., to control the above components), and a power source 210 (e.g., to power the above components). While described as control inputs 208, in some examples, the control inputs 208 may also comprise output devices, such as, for example, audio output devices (e.g., speaker(s)) and/or haptic output devices. While shown as being retained on an external surface of the smart helmet 200 in the example of FIGS. 2a-2b, in some examples, lights 206 and/or control inputs 208 (e.g., microphones) may also be retained on an internal surface of the smart helmet 200. As shown in FIG. 2b, sensors 204 may also be positioned within the helmet shell 230.

In some examples, one or more of the sensors 204 may comprise an optical sensor (e.g., a camera), an inertial measurement unit (IMU) (e.g., comprising an accelerometer and/or gyroscope), a photodiode sensor, a capacitive sensor, an infra-red (IR) sensor, an acoustic sensor, an induction sensor, a motion sensor, an opacity sensor, a proximity sensor, an inductive sensor, a magnet, a magnetic sensor, a GPS sensor, a heat sensor, a thermocouple, a thermistor, a photoelectric sensor, an ultrasonic sensor, an inclinometer, a force sensor, a piezoelectric sensor, a chemical sensor, an ozone sensor, a smoke sensor, a magnetometer, a carbon dioxide detector, a carbon monoxide detector, an oxygen sensor, a glucose sensor, an altimeter, an object detector, a marker detector, a laser rangefinder, a sonar, a heart rate sensor, a current sensor, a voltage sensor, a power sensor, a mechanical switch, a reed switch, a potentiometer, an (e.g., optical) encoder, and/or a gaze tracker.

In some examples, one or more of the sensors 204 may be used to detect whether the helmet is being worn raised, lowered, or not at all. In some examples, one or more of the sensors 204 may be used to automatically identify an operator 102 wearing the smart helmet 200. In some examples, one or more of the sensors 204 (e.g., optical sensor(s)) may be used to record text, image, video, and/or voice messages (e.g., in conjunction with one or more control inputs 208).

While five sensors are shown in the examples of FIGS. 2a-2b, in some examples, more or fewer sensors 204 may be used. In the example of FIG. 2b, at least one sensor 204 is shown within (and/or at/on an internal surface of) the helmet shell 230, though, in some examples, more sensors 204 may be positioned within the helmet shell 230. As shown, the sensor 204 is proximate the thermally conductive element 212, which extends from an external surface of the smart helmet 200 (and/or helmet shell 230) to an internal surface of the smart helmet 200 (and/or helmet shell 230). In some examples, this arrangement may allow the sensor 204 to measure a temperature indicative of the temperature at/of the external surface of the smart helmet 200 (and/or helmet shell 230) without actually being at/on the external surface of the smart helmet 200 and/or subjected to the heat at/on the external surface of the smart helmet 200 (and/or helmet shell 230). In some examples, the thermally conductive element 212 may extend only partway through the smart helmet 200 (and/or helmet shell 230). Thereby, the smart helmet 200 (and/or helmet shell 230) may insulate any heat conducted by the thermally conductive element 212, and prevent the heat from being felt by the operator. In such an example, the sensor 204 may also be positioned within the interior of the smart helmet 200 (and/or helmet shell 230), proximate the thermally conductive element 212.

In the example of FIGS. 2a-2b, the cover lens 202 is positioned in the smart helmet 200 at approximately eye level. As shown, sensors 204 are positioned proximate the cover lens 202. In some examples, the cover lens 202 includes an auto-darkening filter (ADF). In some examples, one or more sensors 104 may be integrated with the cover lens 202 and/or ADF. In some examples, the cover lens 202 may be (e.g., partially or fully) transparent and/or configured to allow an operator 102 to see through the cover lens 202 and view the surrounding environment.

In the example of FIG. 2b, the operator 102 is wearing smart glasses 250 underneath the smart helmet 200. In some examples, the smart glasses 250 may be considered part of the smart helmet 200. While shown as separate from the smart helmet 200 in the example of FIG. 2b, in some examples, the smart glasses 250 may be attached to and/or integrated into the smart helmet 200. While discussed herein as smart glasses 250, in some examples, the smart glasses 250 may actually be goggles, monocles, and/or other eyewear and/or headwear.

In some examples, the smart glasses may include one or more display screens overlaid onto part of the lens(es) of the smart glasses 250. In some examples, a display screen may be part of an entire lens. In some examples, a display screen may be part of only a portion of a lens, so as to be visible to only one eye and/or positioned over a portion (e.g., top/bottom/left/right) of one or both eyes. In some examples, the display screen(s) may be a near-eye display. In some examples, the display screen(s) may be semi-transparent and/or configured to overlay information (e.g., virtual/simulated/holographic objects, guidance, messages, parameters, etc.) onto at least part of lens(es). In some examples, information overlaid via the display screen may include remaining power (e.g., battery life) of the smart helmet 200, status of nearby welding equipment 106 in communication with the smart helmet 200, status of a nearby PAPR (e.g., filter status) in communication with the smart helmet 200, and/or information (e.g., metrics, instructions, guidance, etc.) from weld and/or part tracking systems in communication with the smart helmet 200.

In some examples, one or more optical sensors 204 may be configured to capture images/videos of the surrounding environment, and those images/videos may be processed (e.g., by the helmet circuitry 300) to provide images/videos to the operator 102 via the display screen(s) of the smart glasses 250. In some examples, the smart glasses 250 may include its own sensors (e.g., similar to the sensors 204) and/or circuitry (e.g., similar to the helmet circuitry 300). In some examples, the display screen(s) of the smart glasses 250 may be configured to convert electrical signals (e.g., from the helmet circuitry 300, circuitry of smart glasses 250, sensors of smart glasses 250, and/or sensors 204) into optical information viewable by the operator 102. In some examples, by using display screen to superimpose information onto the smart glasses 250, the operator 102 may be shown a variety of mixed, virtual, and/or augmented reality views, displays, information, and/or interfaces, such as described, for example, in U.S. Pat. No. 10,448,692, issued on Oct. 22, 2019, and U.S. Pat. No. 10,380,911, issued on Aug. 13, 2019, the entirety of both being hereby incorporated by reference.

In some examples, the display screen(s) of the smart glasses 250 may be further configured to show an operator 102 other information. For example, the display screen(s) of the smart glasses 250 may show one or more menus, instructions (e.g., work instructions), welding parameters (e.g., voltage, current, wire feed speed, etc.) of the welding equipment 106, settings of the smart glasses 250, properties of the cover lens 202 (e.g., ADF mode, shade, sensitively, delay settings), settings of the smart helmet 200, trigger lock settings of the welding torch 114, consumable status of the welding torch 114 and/or wire feeder 120, fume extraction information, maintenance information, messages (e.g., text, video, image, etc.), alerts, notifications, times (e.g., duration of last weld, arc on time for day, week, all time, etc.), and/or other information. In some examples, information displayed via the display screen(s) may be pinned and/or anchored to one or more real world locations. In some examples, the smart glasses 250 may be further configured to zoom, pan, crop and/or otherwise adjust how content is shown on the display screen(s) of the smart glasses 250.

In some examples, the smart glasses 250 may include one or more control inputs and/or control outputs (e.g., speakers, microphones, touchpad, buttons, etc.), such as, for example, on the frame of the smart glasses 250. However, as the smart glasses 250 may be difficult for an operator 102 to access while wearing the smart welding helmet 200, in some examples, the smart helmet 200 may be configured to receive inputs via the control inputs 208 of the smart helmet 200 and relay the inputs (as appropriate) to the smart glasses 250 as if they were inputs of the smart glasses 250 themselves. In some examples, the smart glasses 250 may include communication circuitry configured to communicate with the smart helmet 200 via one or more wired and/or wireless protocols, such as discussed below.

Figure 3:
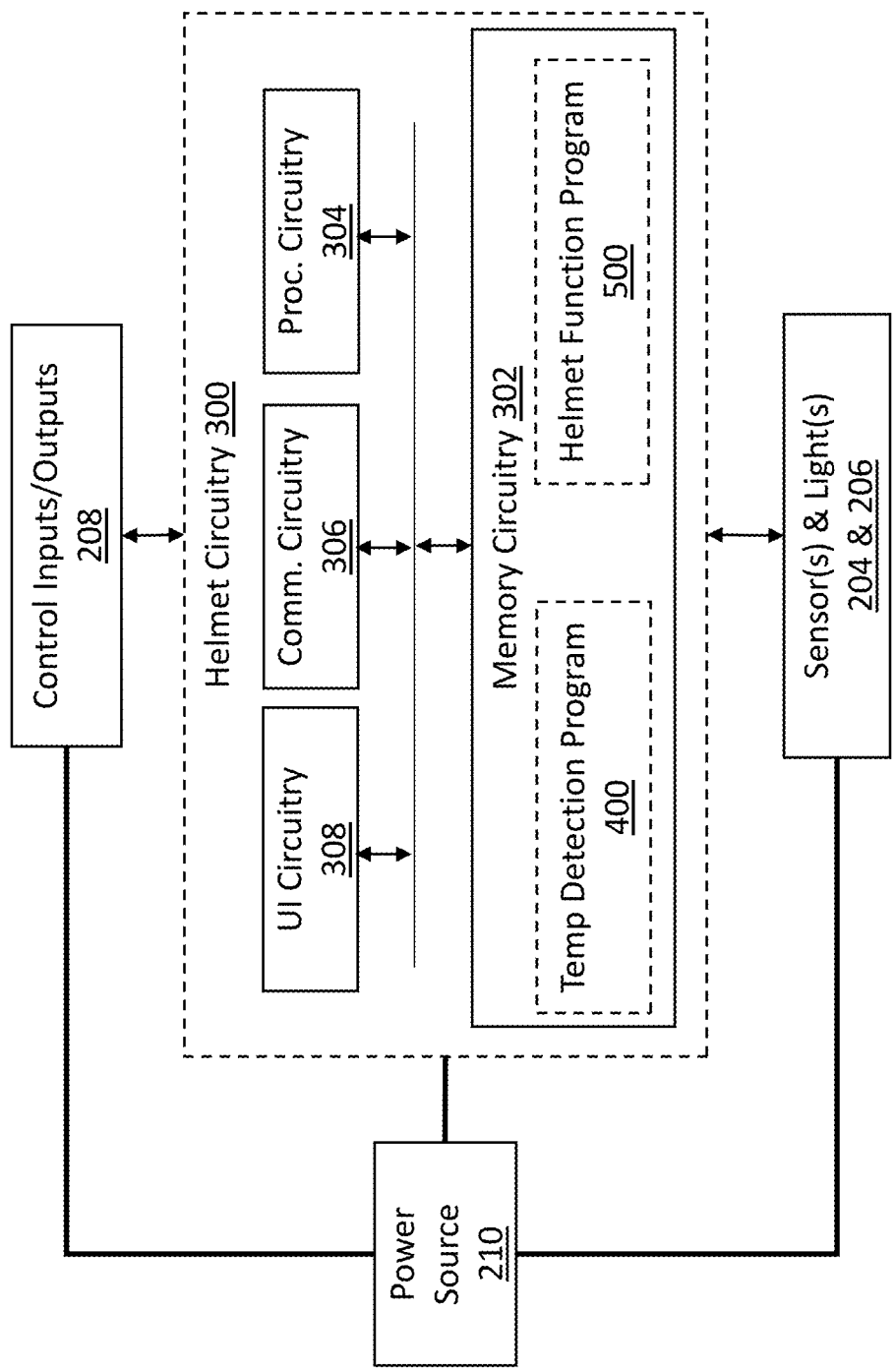
FIG. 3 is a block diagram showing example electrical components of the smart helmet of FIG. 1, in accordance with aspects of this disclosure.

FIG. 3 is a block diagram showing example components of the helmet circuitry 300 of the smart helmet 200, as well as interconnections between the components of the helmet circuitry 300 and other components of the smart helmet 200. As shown, the helmet circuitry 300 includes memory circuitry 302, processing circuitry 304, communication circuitry 306, and user interface (UI) circuitry 308, interconnected with one another via a common electrical bus. The helmet circuitry 300 is also in electrical communication with the control inputs/outputs 208, the sensor(s) 204, and the light(s) 206.

In the example of FIG. 3, the helmet circuitry 300, control inputs/outputs 208, sensor(s) 204, and light(s) 206 are powered by a power source 210 (e.g., a battery, power cell, etc.). While the power source 210, sensor(s) 204, and light(s) 206 are shown as separate from the helmet circuitry 300 in the example of FIG. 3, in some examples, the power source 210 and/or some or all of the sensors 204 and/or lights 206 may be part of the helmet circuitry 300. In some examples, one or more of the sensors 204 may be configured to detect a remaining power (and/or voltage) level of the power source 210, and/or a current output power (and/or current/ voltage) of the power source 210. In some examples, the power source 210 may be configured to connect to and/or receive power from an external source, either to directly power the smart helmet 200 or to recharge the power source 210 (e.g., via wired or wireless recharging).

In some examples, the UI circuitry 308 may be coupled to the control inputs 208 (and/or certain mechanical and/or electromechanical aspects of the control inputs 208). In some examples, the UI circuitry 308 may comprise one or more drivers for the control inputs 208. In some examples, the UI circuitry 308 may be configured to generate one or more signals representative of input received via the control inputs 208. In some examples, the UI circuitry 308 may also be configured to generate one or more outputs (e.g., via the via the control inputs 208) in response to one or more signals (e.g., received via the bus).

In some examples, the communication circuitry 306 may include one or more wireless adapters, wireless cards, cable adapters, wire adapters, dongles, radio frequency (RF) devices, wireless communication devices, Bluetooth devices, IEEE 802.11-compliant devices, WiFi devices, cellular devices, GPS devices, Ethernet ports, network ports, lightning cable ports, cable ports, etc. In some examples, the communication circuitry 306 may be configured to facilitate communication via one or more wired media and/or protocols (e.g., Ethernet cable(s), universal serial bus cable(s), etc.) and/or wireless mediums and/or protocols (e.g., cellular communication, general packet radio service (GPRS), near field communication (NFC), ultra high frequency radio waves (commonly known as Bluetooth), IEEE 802.11x, Zigbee, HART, LTE, Z-Wave, WirelessHD, WiGig, etc.). In some examples, the communication circuitry 306 may be coupled to one or more antennas to facilitate wireless communication.

In some examples, the communication circuitry 306 may be configured to facilitate communications between the smart helmet 200 and other devices internal to, and/or external of, the smart helmet 200. For example, the communication circuitry 306 of the smart helmet 200 may facilitate communications between the smart helmet 200 and the smart glasses 250, other smart helmets 200, one or more mobile devices 101, the remote server(s) 108, the welding equipment 106, and/or other devices. In some examples, the communication circuitry 306 may receive one or more signals (e.g., from the welding equipment 106, sensor(s) 204, remote server(s) 108, cover lens 202, etc.) decode the signal(s), and provide the decoded data to the electrical bus. As another example, the communication circuitry 306 may receive one or more signals from the electrical bus (e.g., representative of one or more inputs from control inputs 208) encode the signal(s), and transmit the encoded signal(s) to an external device (e.g., the smart glasses 250, other smart helmets 200, one or more mobile devices 101, the remote server(s) 108, the welding equipment 106, etc.).

In some examples, the processing circuitry 304 may comprise one or more processors, controllers, and/or graphical processing units (GPUs). In some examples, the processing circuitry 304 may comprise one or more drivers for the sensor(s) 204 and/or cover lens 202. In some examples, the processing circuitry 304 may be configured to execute machine readable instructions stored in the memory circuitry 302.

In the example of FIG. 3, the memory circuitry 302 includes (and/or stores) a temperature detection program 400 and a helmet function program 500. In some examples, the temperature detection program 400 and helmet function program 500 may comprise machine readable instructions configured for execution by the processing circuitry 304. In some examples, the temperature detection program 400 and the helmet function program 500 may be implemented via discrete circuitry (e.g., of the processing circuitry 304) rather than, or in addition to, being part of (and/or stored in) the memory circuitry 302.

In some examples, the temperature detection program 400 may take action if/when a detected temperature of the smart helmet 200 exceeds one or more threshold temperatures. In some examples, the temperature detection program 400 may run continuously while the temperature detection program 400 is enabled and/or the smart helmet 200 is powered on and/or activated. In some examples, the temperature detection program 400 may run only during welding operations. For example, the smart helmet 200 may receive one or more signals from the welding torch 114 and/or welding equipment 106 indicating that a welding operation is occurring (e.g., via indicative values of voltage, current, wire feed speed, and/or other welding parameters), and activate the temperature detection program 400 in response to determining a welding operation is occurring.

Figure 4:
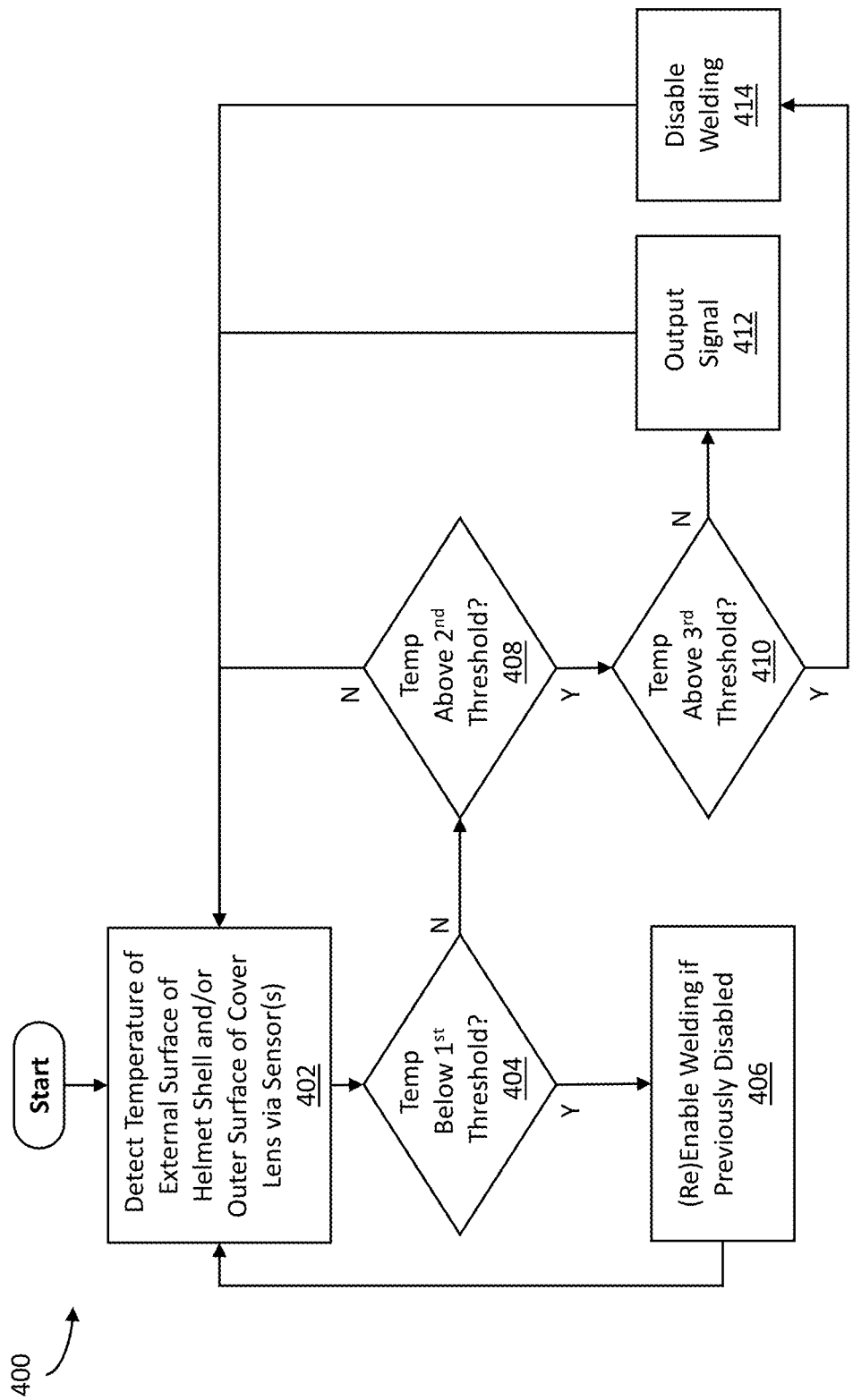
FIG. 4 is a flow diagram illustrating an example operation of a temperature detection program of the smart helmet of FIG. 1, in accordance with aspects of this disclosure.

FIG. 4 is a flowchart illustrating operation of an example temperature detection program 400. In the example of FIG. 4, the temperature detection program 400 begins at block 402, where the temperature detection program 400 detects a temperature of the smart welding helmet 200. In particular, the temperature detection program 400 may detect a temperature of an external surface of the helmet shell 230 and/or an outer surface of the cover lens 202 of the smart helmet 200 via sensor(s) 204. In some examples, one or more sensors 204 positioned at/on the exterior surface of helmet shell 230, and/or proximate to the cover lens 202, may be used to measure the temperature. In some examples, one or more sensors 204 positioned at/on an interior surface of the helmet shell 230 may measure a temperature indicative of the temperature of the external surface of the helmet shell 230 and/or an outer surface of the cover lens 202 via the thermally conductive element 212.

In the example of FIG. 4, the temperature detection program 400 proceeds to block 404 after block 402. At block 404, the temperature detection program 400 compares the temperature measured at block 402 to a first threshold temperature. In some examples, the first threshold temperature may be stored in memory circuitry 302 and/or set by the operator 102 (e.g., via the control inputs 208). In some examples, the first threshold temperature may be relatively low temperature below which there is little risk to the smart helmet 200.

In the example of FIG. 4, the temperature detection program 400 proceeds to block 406 after block 404 if the measured temperature from block 402 is below the first threshold temperature. At block 406, the temperature detection program 400 enables (and/or re-enables) the welding equipment 106, to the extent necessary. In some examples, block 406 may only execute if the temperature detection program 400 previously disabled the welding equipment 106 (without enabling afterwards). In some examples, the temperature detection program 400 may enable the welding equipment 106 by sending one or more enable signals to the welding equipment 106 (e.g., via the communication circuitry 306).

In the example of FIG. 4, the temperature detection program 400 proceeds to block 408 after block 404 if the measured temperature from block 402 is not below the first threshold temperature. At block 408 the temperature detection program 400 compares the temperature measured at block 402 to a second threshold temperature. In some examples, the second threshold temperature may be the same as the first threshold temperature. In some examples, the second threshold temperature may be higher than the first threshold temperature. In some examples, the second threshold temperature may be stored in memory circuitry 302 and/or set by the operator 102 (e.g., via the control inputs 208). In some examples, the second threshold temperature may be a temperature above which there is a risk of damage to the helmet shell 230 and/or cover lens 202 (e.g., due to extreme heat and/or melting). As shown, the temperature detection program 400 returns to block 402 after block 408 if the measured temperature is not greater than the second threshold temperature.

In the example of FIG. 4, the temperature detection program 400 proceeds to block 410 after block 408 if the measured temperature is greater than the second threshold temperature. At block 410, the temperature detection program 400 compares the temperature measured at block 402 to a third threshold temperature. In some examples, the third threshold temperature may be the same as the second threshold temperature. In some examples, the third threshold temperature may be higher than the second threshold temperature. In some examples, the third threshold temperature may be stored in memory circuitry 302 and/or set by the operator 102 (e.g., via the control inputs 208). In some examples, the third threshold temperature may be a temperature above which there is an imminent and high risk of damage to the helmet shell 230 and/or cover lens 202 due to the detected heat.

In the example of FIG. 4, the temperature detection program 400 proceeds to block 412 after block 410 if the measured temperature is not greater than the third threshold temperature. In some examples, the temperature detection program 400 may proceed to block 412 after block 408 if the measured temperature is greater than the second threshold temperature (and then to block 410 after block 412). At block 412, the temperature detection program 400 outputs one or more signals. For example, the signal(s) may be representative of a notification to the operator 102 that the temperature of the helmet shell 230 and/or cover lens 202 has exceeded the second threshold temperature.

In some examples, the signal(s) may be output via the control inputs/outputs 208 and/or smart glasses 250. For example, the notification may be output to the operator 102 via the display screen(s) of the smart glasses 250, speakers of the smart glasses 250, speakers of the control inputs/outputs 208, and/or some other appropriate mechanism. In some examples, the signal(s) may be output via the helmet communication circuitry 306 of the smart helmet 200. For example, the helmet communication circuitry 306 may send the signal(s) to one or more mobile devices 101 (e.g., of the operator 102, supervisor(s), etc.), remote servers 108, other smart helmets 200, and/or other devices. As shown, the temperature detection program 400 returns to block 402 after block 412.

In the example of FIG. 4, the temperature detection program 400 proceeds to block 414 after block 410 if the measured temperature is greater than the third threshold temperature. At block 414, the temperature detection program 400 disables the welding equipment 106 (e.g., welding-type power supply 118 and/or wire feeder 120) and/or welding torch 114, so as to prevent the temperature of the smart helmet 200 from further increasing. In some examples, the temperature detection program 400 may disable the welding equipment 106 and/or welding torch 114 by sending one or more disable signals to the welding equipment 106 and/or welding torch 114. In some examples, in response to receiving the signal(s), the control circuitry 126 may stop the motor from feeding additional wire and/or control the power conversion circuitry 128 to cease outputting welding-type power. In some examples, in response to receiving the signal(s), the welding torch 114 may cease sending trigger signals to the welding equipment 106 and/or applying welding-type power via a torch electrode. As shown, the temperature detection program 400 returns to block 402 after block 414.

FIG. 5 is a flowchart illustrating operation of an example helmet function program 500. In some examples, the helmet function program 500 may selectively enable and/or disable certain functions of the smart welding helmet 500 to accommodate different operators 102. In some examples, the helmet function program 500 may run continuously while the smart helmet 200 is powered on and/or activated. In some examples, the helmet function program 500 may execute at startup, login, and/or initialization.

In the example of FIG. 5, the helmet function program 500 begins at block 502. At block 502, the helmet function program 500 identifies the smart helmet 200 and/or the operator 102 wearing the smart helmet 200. For example, the smart helmet 200 may store in memory circuitry 302 a unique identifier (e.g., serial number) of the smart helmet 200. As another example, the smart helmet 200 may receive identifying information from the operator (e.g., via the control inputs 208) and/or detect identifying information of the operator (e.g., via sensor(s) 204). In some examples, an operator 102 may provide identifying information correlated with administrative (e.g., total) access, rather than any particular operator. In some examples, block 502 may be skipped altogether.

In the example of FIG. 5, the helmet function program 500 proceeds to block 504 after block 502. At block 504, the helmet function program 500 identifies which functions of the smart helmet 200 are accessible to this particular operator 102 and/or smart helmet 200. In some examples, the smart helmet 200 may make this identification by accessing one or more files and/or data structures in memory circuitry 302. For example, there may be a file and/or data structure in memory circuitry 302 that correlates particular operators 102 and/or smart helmets 200 with a list of accessible and/or inaccessible helmet functions. As another example, the file and/or data structure may pertain to just one particular smart helmet 200.

In some examples, the identification of accessible helmet functions may involve communication (e.g., via helmet communication circuitry 306) with one or more external devices, such as, for example, the remote server(s) 108. For example, the smart helmet 200 may send one or more signals (e.g., representative of the identification information of block 502) to the remote server(s) 108 and receive, in response, one or more signals representative of the accessible and/or inaccessible helmet functions for the operator 102 and/or smart helmet 200.

In some examples, a helmet function may be a capability of the smart helmet 200 that can be enabled and/or disabled by the smart helmet 200, such as, for example, a productivity and/or quality enhancement feature. For example, one helmet function may be an ability for the smart helmet 200 to detect a status of the smart helmet 200 (e.g., whether the smart helmet 200 is being worn, and/or worn in an up/down position), such as via sensor(s) 204. As another example, a helmet function may include an ability of the smart helmet 200 to automatically configure the light(s) 206 of the smart helmet 200, such as depending on whether an arc is present and/or the status of the smart helmet 200. Another example of a helmet function might be the ability to automatically configure the cover lens 202 and/or one or more lenses of the smart glasses 250 (e.g., based on some input and/or saved operator preferences). Another example of a helmet function might be the ability to detect (e.g., via sensor(s) 204), determine, and/or display (or otherwise output) a travel speed of the welding torch 114. Another example of a helmet function might be the temperature detection program 400. Another example of a helmet function might be the ability to detect (e.g. via sensor(s) 204) whether personal protective equipment (PPE) is being worn by the operator 102. Another example of a helmet function might be the ability to track (e.g., via sensor(s) 204 and/or communication with the torch 114 and/or welding equipment 106) an amount of time a welding operation takes place and/or a welding arc is present in proximity to the operator 102. Another example of a helmet function might be the ability to automatically identify (e.g., via sensor(s) 204) an identity of the operator 102. Another example of a helmet function might be the ability to detect (e.g. via sensor(s) 204) whether the cover lens 202 needs replacement and/or maintenance. Another example of a helmet function might be the ability to communicate with the welding torch 114, welding equipment 106, remote server(s) 108, mobile device(s) 101, and/or other smart helmets 200. Other examples of helmet functions might include the ability to view (e.g., via smart glasses 250) work instructions, parameters of the welding equipment 106, real time welding technique guidance/feedback, and/or other pertinent information.

In the example of FIG. 5, the helmet function program 500 proceeds to block 506 after block 504. At block 506, the helmet function program 500 outputs one or more signals to inform the operator 102 of the helmet functions to which they have (and/or do not have) access, based on the identification(s) of block 504. In some examples, the helmet function program 500 may inform the operator 102 by outputting one or more signals representative of helmet functions to which they have (and/or do not have) access. In some examples, the signal(s) may be sent to the smart glasses 250 and/or control inputs/outputs 208, which may provide output(s) informing the operator 102. In some examples, the signal(s) may be output via the helmet communication circuitry 306 of the smart helmet 200. For example, the helmet communication circuitry 306 may send the signal(s) to one or more mobile devices 101 (e.g., of the operator 102, supervisor(s), etc.), remote servers 108, other smart helmets 200, and/or other devices.

In the example of FIG. 5, the helmet function program 500 proceeds to block 508 after block 506. At block 508, the helmet function program 500 determines whether to change which helmet functions are currently accessible/inaccessible. In some examples, this determination may be based on user input (e.g., via control inputs 208). In some examples, the helmet function program 500 may prompt the operator 102 for input as to whether they would like to change which helmet functions are currently accessible/inaccessible.

In the example of FIG. 5, the helmet function program 500 proceeds to block 510 after block 508 if the helmet function program 500 determines not to change which helmet functions are currently accessible/inaccessible. At block 510, the helmet function program 500 enables those helmet functions that were identified as accessible, and disables those helmet functions identified as inaccessible. As shown, the helmet function program 500 ends after block 510.

In the example of FIG. 5, the helmet function program 500 proceeds to block 512 after block 508 if the helmet function program 500 determines to change which helmet functions are currently accessible/inaccessible. At block 512 the helmet function program 500 facilitates desired changes to which helmet functions are accessible/inaccessible for the operator 102 and/or smart welding helmet 200. In some examples, the helmet function program 500 may communicate and/or interact with the remote server(s) 108 to facilitate the change(s). In some examples, facilitating the change(s) may involve facilitating one or more (e.g., financial) transactions. In some examples, an operator may provide a code and/or identifier correlated with a previously obtained credit, access level, class designation, job, etc. that may be correlated with certain accessible and/or inaccessible helmet functions. In some examples, changes may also be made to which helmet functions are accessible/inaccessible outside of the helmet function program 500, such as through interaction (e.g. via mobile device 101) with one or more websites and/or portals hosted by the remote server(s) 108.

In the example of FIG. 5, the helmet function program 500 proceeds to block 514 after block 512. At block 514, the helmet function program 500 updates one or more files and/or databases in/at the remote server(s) 108 and/or the memory circuitry 302 of the smart helmet 200 based on the changes made at block 512. In some examples, this update may involve changing the identification of some helmet functions as accessible/inaccessible. As shown, the helmet function program 500 returns to block 504 after block 514.

The disclosed smart welding helmet 200 has a plurality of functionalities that go beyond conventional welding helmets. For example, the smart welding helmet 200 has the ability to detect if/when an external surface of the helmet shell 230 and/or outer surface of the cover lens 202 exceed one or more temperature thresholds, and react accordingly. The smart welding helmet 200 can also selectively enable/disable certain functions of the smart welding helmet 200 to accommodate the needs of a particular operator 102 and/or groups of operators 102.

The present methods and/or systems may be realized in hardware, software, or a combination of hardware and software. The present methods and/or systems may be realized in a centralized fashion in at least one computing system, or in a distributed fashion where different elements are spread across several interconnected computing or cloud systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

As used herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z".

As utilized herein, the terms "e.g.," and "for example" set off lists of one or more non-limiting examples, instances, or illustrations.

As used herein, the terms "coupled," "coupled to," and "coupled with," each mean a structural and/or electrical connection, whether attached, affixed, connected, joined, fastened, linked, and/or otherwise secured. As used herein, the term "attach" means to affix, couple, connect, join, fasten, link, and/or otherwise secure. As used herein, the term "connect" means to attach, affix, couple, join, fasten, link, and/or otherwise secure.

As used herein the terms "circuits" and "circuitry" refer to physical electronic components (i.e., hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, circuitry is "operable" and/or "configured" to perform a function whenever the circuitry comprises the necessary hardware and/or code (if any is necessary) to perform the function, regardless of whether performance of the function is disabled or enabled (e.g., by a user-configurable setting, factory trim, etc.).

As used herein, a control circuit may include digital and/or analog circuitry, discrete and/or integrated circuitry, microprocessors, DSPs, etc., software, hardware and/or firmware, located on one or more boards, that form part or all of a controller, and/or are used to control a welding process, and/or a device such as a power source or wire feeder.

As used herein, the term "processor" means processing devices, apparatus, programs, circuits, components, systems, and subsystems, whether implemented in hardware, tangibly embodied software, or both, and whether or not it is programmable. The term "processor" as used herein includes, but is not limited to, one or more computing devices, hardwired circuits, signal-modifying devices and systems, devices and machines for controlling systems, central processing units, programmable devices and systems, field-programmable gate arrays, application-specific integrated circuits, systems on a chip, systems comprising discrete elements and/or circuits, state machines, virtual machines, data processors, processing facilities, and combinations of any of the foregoing. The processor may be, for example, any type of general purpose microprocessor or microcontroller, a digital signal processing (DSP) processor, an application-specific integrated circuit (ASIC), a graphic processing unit (GPU), a reduced instruction set computer (RISC) processor with an advanced RISC machine (ARM) core, etc. The processor may be coupled to, and/or integrated with a memory device.

As used, herein, the term "memory" and/or "memory device" means computer hardware or circuitry to store information for use by a processor and/or other digital device. The memory and/or memory device can be any suitable type of computer memory or any other type of electronic storage medium, such as, for example, read-only memory (ROM), random access memory (RAM), cache memory, compact disc read-only memory (CDROM), electro-optical memory, magneto-optical memory, programmable read-only memory (PROM), erasable programmable read-only memory (EPROM), electrically-erasable programmable read-only memory (EEPROM), a computer-readable medium, or the like. Memory can include, for example, a non-transitory memory, a non-transitory processor readable medium, a non-transitory computer readable medium, non-volatile memory, dynamic RAM (DRAM), volatile memory, ferroelectric RAM (FRAM), first-in-first-out (FIFO) memory, last-in-first-out (LIFO) memory, stack memory, non-volatile RAM (NVRAM), static RAM (SRAM), a cache, a buffer, a semiconductor memory, a magnetic memory, an optical memory, a flash memory, a flash card, a compact flash card, memory cards, secure digital memory cards, a microcard, a minicard, an expansion card, a smart card, a memory stick, a multimedia card, a picture card, flash storage, a subscriber identity module (SIM) card, a hard drive (HDD), a solid state drive (SSD), etc. The memory can be configured to store code, instructions, applications, software, firmware and/or data, and may be external, internal, or both with respect to the processor.

The term "power" is used throughout this specification for convenience, but also includes related measures such as energy, current, voltage, and enthalpy. For example, controlling "power" may involve controlling voltage, current, energy, and/or enthalpy, and/or controlling based on "power" may involve controlling based on voltage, current, energy, and/or enthalpy.

As used herein, welding-type power refers to power suitable for welding, cladding, brazing, plasma cutting, induction heating, carbon arc cutting, and/or hot wire welding/preheating (including laser welding and laser cladding), carbon arc cutting or gouging, and/or resistive preheating.

As used herein, a welding-type power supply and/or power source refers to any device capable of, when power is applied thereto, supplying welding, cladding, brazing, plasma cutting, induction heating, laser (including laser welding, laser hybrid, and laser cladding), carbon arc cutting or gouging, and/or resistive preheating, including but not limited to transformer-rectifiers, inverters, converters, resonant power supplies, quasi-resonant power supplies, switchmode power supplies, etc., as well as control circuitry and other ancillary circuitry associated therewith.

As used herein, disable may mean deactivate, incapacitate, and/or make inoperative. As used herein, enable may mean activate and/or make operational.

Disabling of circuitry, actuators, and/or other hardware may be done via hardware, software (including firmware), or a combination of hardware and software, and may include physical disconnection, de-energization, and/or a software control that restricts commands from being implemented to activate the circuitry, actuators, and/or other hardware. Similarly, enabling of circuitry, actuators, and/or other hardware may be done via hardware, software (including firmware), or a combination of hardware and software, using the same mechanisms used for disabling.

What is claimed is:

1. A welding helmet, comprising:
  a helmet shell having a helmet shell exterior and a helmet shell interior, the helmet shell exterior comprising a first helmet shell external surface and a second helmet shell external surface that is connected to, and positioned on an opposite side of the helmet shell interior from, the first helmet shell external surface;
  a cover lens having an outer surface;
  a thermal conductor extending partway through the helmet shell into the helmet shell interior, such that the thermal conductor extends through the first helmet shell external surface but does not extend through the second helmet shell external surface;

a temperature sensor configured to measure a temperature of the thermal conductor within the helmet shell interior; and control circuitry configured to output a signal in response to determining the temperature exceeds a temperature threshold.

2. The welding helmet of claim 1, wherein the thermal conductor comprises an interior thermal conductor and an exterior thermal conductor that is thermally connected to the interior thermal conductor, the interior thermal conductor being positioned within the helmet shell interior, and the exterior thermal conductor being positioned outside of the helmet shell interior, proximate to the outer surface of the cover lens, the temperature sensor being positioned within the helmet shell interior proximate to the interior thermal conductor.

3. The welding helmet of claim 1, wherein the welding helmet further comprises a user interface configured to receive the signal and output a visual notification or audible notification in response to receiving the signal.

4. The welding helmet of claim 3, wherein the temperature threshold comprises a first temperature threshold, the signal comprises a notification signal, and the control circuitry is further configured to output a disable signal to a welding-type power supply, a welding torch, or a welding wire feeder, via communication circuitry of the welding helmet, in response to determining the temperature exceeds a second temperature threshold.

5. The welding helmet of claim 4, wherein the second temperature threshold is higher than the first temperature threshold.

6. The welding helmet of claim 5, wherein the control circuitry is configured to output an enable signal to the welding-type power supply, the welding torch, or the welding wire feeder, via the communication circuitry, in response to determining the temperature is less than a third temperature threshold.

7. The welding helmet of claim 6, wherein the third temperature threshold is less than the first temperature threshold and the second temperature threshold.

8. The welding helmet of claim 1, wherein the signal comprises a disable signal, and the control circuitry is configured to output the disable signal, via communication circuitry of the welding helmet, to a welding-type power supply, a welding torch, or a welding wire feeder, via communication circuitry of the welding helmet.

9. The welding helmet of claim 8, wherein the temperature threshold comprises a first temperature threshold, the control circuitry being configured to output an enable signal to the welding-type power supply, the welding torch, or the welding wire feeder, via the communication circuitry, in response to determining the temperature is less than a second temperature threshold.

10. The welding helmet of claim 9, wherein the second temperature threshold is less than the first temperature threshold.

11. A welding helmet, comprising:
a helmet shell having a helmet shell interior sandwiched between a first helmet shell exterior surface and second helmet shell exterior surface;

a thermal conductor extending partway through the helmet shell into the helmet shell interior, such that the thermal conductor extends through the first helmet shell exterior surface but does not extend through the second helmet shell exterior surface, the thermal conductor comprising an interior thermal conductor and an exterior thermal conductor that is thermally connected with the interior thermal conductor, the interior thermal conductor being positioned within the helmet shell interior, and the exterior thermal conductor being positioned outside of the helmet shell interior; and a temperature sensor positioned within the helmet shell interior, the temperature sensor being configured to measure a temperature of the interior thermal conductor.

12. The welding helmet of claim 11, further comprising control circuitry configured to output a signal in response to determining the temperature exceeds a temperature threshold.

13. The welding helmet of claim 12, wherein the welding helmet further comprises a user interface configured to receive the signal and output a visual notification or audible notification in response to receiving the signal.

14. The welding helmet of claim 13, wherein the temperature threshold comprises a first temperature threshold, and the signal comprises a notification signal, the control circuitry being further configured to output a disable signal to a welding-type power supply or a welding wire feeder, via communication circuitry of the welding helmet, in response to determining the temperature exceeds a second temperature threshold.

15. The welding helmet of claim 14, wherein the second temperature threshold is higher than the first temperature threshold.

16. The welding helmet of claim 15, wherein the control circuitry is configured to output an enable signal to the welding-type power supply or the welding wire feeder, via the communication circuitry, in response to determining the temperature is less than a third temperature threshold.

17. The welding helmet of claim 16, wherein the third temperature threshold is less than the first temperature threshold and second temperature threshold.

18. The welding helmet of claim 12, wherein the signal comprises a disable signal, and the control circuitry is configured to output the disable signal to a welding-type power supply or a welding wire feeder, via communication circuitry of the welding helmet.

19. The welding helmet of claim 18, wherein the temperature threshold comprises a first temperature threshold, the control circuitry being configured to output an enable signal to the welding-type power supply or the welding wire feeder, via the communication circuitry, in response to determining the temperature is less than a second temperature threshold.

20. The welding helmet of claim 19, wherein the second temperature threshold is less than the first temperature threshold.

\* \* \* \* \*